(12) United States Patent
Hanebuchi (10) Patent No.: US 7,434,932 B2
(45) Date of Patent: Oct. 14, 2008

(54) OPHTHALMIC APPARATUS

(75) Inventor: Masaaki Hanebuchi, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 34 days.

(21) Appl. No.: 11/477,665

(22) Filed: Jun. 30, 2006

(65) Prior Publication Data

US 2007/0002277 A1  Jan. 4, 2007

(30) Foreign Application Priority Data

| Jul. 1, 2005 | (JP) | 2005-194456 |
| Jul. 1, 2005 | (JP) | 2005-194457 |
| May 29, 2006 | (JP) | 2006-148420 |

(51) Int. Cl.
*A61B 3/14* (2006.01)

(52) U.S. Cl. .......... 351/206; 351/212; 351/221; 351/205; 351/200

(58) Field of Classification Search .......... 351/221, 351/212, 205, 200, 206
See application file for complete search history.

(56) References Cited

U.S. PATENT DOCUMENTS

| 5,905,572 A * | 5/1999 | Li .................. 356/479 |
| 6,288,784 B1 | 9/2001 | Hitzenberger et al. |
| 6,377,349 B1 | 4/2002 | Fercher |
| 2003/0072007 A1 | 4/2003 | Fercher |
| 2003/0189690 A1 * | 10/2003 | Mihashi et al. ........ 351/221 |

FOREIGN PATENT DOCUMENTS

| AT | 500 501 A1 | 1/2006 |
| DE | 101 42 001 A1 | 3/2003 |
| EP | 1 602 320 A1 | 12/2005 |
| JP | A 7-255674 | 10/1995 |
| JP | A 11-325849 | 11/1999 |
| JP | A 2004-28970 | 1/2004 |
| WO | WO 2004/043245 A1 | 5/2004 |

* cited by examiner

*Primary Examiner*—Ricky Mack
*Assistant Examiner*—James R Greece
(74) *Attorney, Agent, or Firm*—Oliff & Berridge, PLC (57) ABSTRACT

An ophthalmic apparatus capable of obtaining various kinds of ocular information on an examinee's eye by itself without contacting the eye. The ophthalmic apparatus has a first projection optical system which makes first light with short coherence length converge at a fundus of the eye, a second projection optical system which makes second light with short coherence length converge at an anterior segment of the eye, a photo-receiving optical system which synthesizes the first light reflected from the fundus and the second light reflected from the anterior segment into interference light, disperses the interference light into frequency components and photo-receives the dispersed light with a first photodetector, and a calculation part which obtains depth information of the eye as ocular information based on a result obtained by analyzing an output signal from the first photodetector by means of Fourier transform.

12 Claims, 9 Drawing Sheets

OPHTHALMIC APPARATUS

BACKGROUND OF THE INVENTION

1. Field of the Invention

The present invention relates to an ophthalmic apparatus for obtaining ocular information.

2. Description of Related Art

As an ophthalmic apparatus for obtaining ocular information without contacting an eye, conventionally there is an apparatus which performs noncontact measurement of eye refractive power, a corneal radius of curvature and internal dimensions of an eye (see Japanese Patent Application Unexamined Publication No. Hei7-255674). In order to increase efficiency of examination and the like, desired is an apparatus which is capable of obtaining more ocular information by itself.

SUMMARY OF THE INVENTION

An object of the invention is to overcome the problems described above and to provide an ophthalmic apparatus capable of obtaining various kinds of ocular information by itself.

To achieve the objects and in accordance with the purpose of the present invention, an ophthalmic apparatus for obtaining ocular information on an examinee's eye without contacting the eye has a first projection optical system which makes first light with short coherence length converge at a fundus of the eye, a second projection optical system which makes second light with short coherence length converge at an anterior segment of the eye, a photo-receiving optical system which synthesizes the first light reflected from the fundus and the second light reflected from the anterior segment into interference light, disperses the interference light into frequency components and photo-receives the dispersed light with a first photodetector, and a calculation part which obtains depth information of the eye as ocular information based on a result obtained by analyzing an output signal from the first photodetector by means of Fourier transform.

Additional objects and advantages of the invention are set forth in the description which follows, are obvious from the description, or may be learned by practicing the invention. The objects and advantages of the invention may be realized and attained by the ophthalmic apparatus in the claims,

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
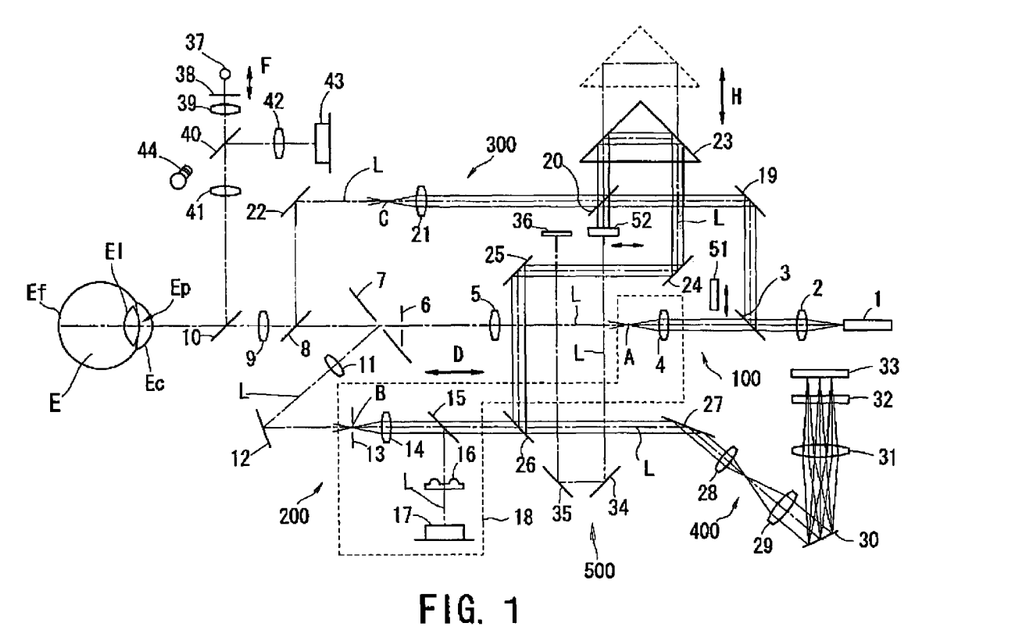
FIG. 1 is a view showing a schematic configuration of an optical system of an ophthalmic apparatus consistent with the preferred embodiment of the present invention.
Figure 2:
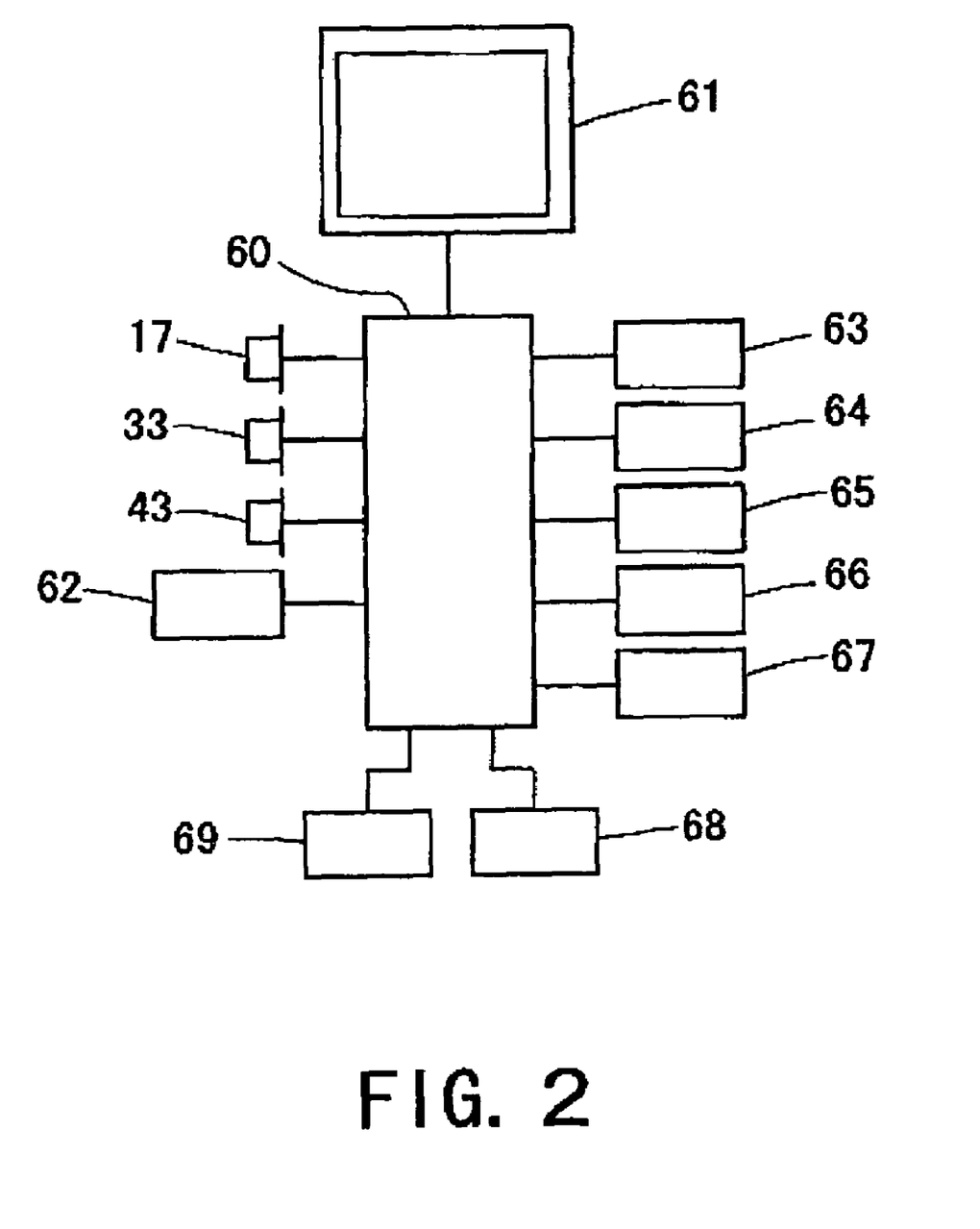
FIG. 2 is a schematic block diagram of a control system of the present apparatus.

A detailed description of one preferred embodiment of an ophthalmic apparatus embodied by the present invention is provided below with reference to the accompanying drawings. FIG. 1 is a view showing a schematic configuration of an optical system of the ophthalmic apparatus consistent with the preferred embodiment of the present invention. FIG. 2 is a schematic block diagram of a control system of the present apparatus. Incidentally, the optical system of the present apparatus includes a projection optical system 100 for eye refractive power measurement and eye depth information obtainment, a photo-receiving optical system 200 for eye refractive power measurement, a projection optical system 300 for eye depth information obtainment, an interference/spectral/photo-receiving optical system (interference-signal detecting optical system) 400 for eye depth information obtainment, a reference-light forming optical system 500 for eye depth information obtainment, a fixation target presenting optical system, and an observation optical system. In addition, the optical system of the present apparatus further includes an alignment optical system for aligning the apparatus to have a predetermined positional relationship with an examinee's eye; however, description thereof is omitted since an optical system similar to a known alignment optical system used in an objective eye refractive power measurement apparatus and the like may be used.

<Projection Optical System 100 for Eye Refractive Power Measurement and Eye Depth Information Obtainment>

The projection optical system 100 includes a light source 1, a collimator lens 2, a half mirror 3, a condenser lens 4, a relay lens 5, a diaphragm 6, a hole mirror 7, a half mirror 8, an objective lens 9, and a half mirror 10. The light source 1 such as a near infrared super luminescent diode (SLD) emits near infrared light with short coherence length, and the light is made into parallel light by the collimator lens 2, and a part thereof passes through the half mirror 3. The light which passed through the half mirror 3 converges at a convergent point A on an optical axis L by the condenser lens 4, and passes through the relay lens 5, the diaphragm 6 and a hole (aperture) of the hole mirror 7 to converge, and a part thereof passes through the half mirror 8. The light which passed through the half mirror 8 passes through the objective lens 9, and a part thereof passes through the half mirror 10. The light which passed through the half mirror 10 converges at a fundus Ef of an examinee's eye E.

On an optical path between the half mirror 3 and the condenser lens 4, an interception plate (shutter) 51 is arranged insertable and removable, which is inserted in and removed from the optical path by a driving unit (driving means) 66, Besides, a position in which the interception plate 51 is arranged is not limited to the above-described position, and it is essential only to arrange the interception plate 51 on an optical path which is singly used for the projection optical system 100 and not shared with the other optical systems to be described later.

<Photo-Receiving Optical System 200 for Eye Refractive Power Measurement>

The photo-receiving optical system 200 includes the half mirror 10, the objective lens 9, the half mirror 8 and the hole mirror 7 which are shared with the projection optical system 100, and a relay lens 11, a total reflection mirror 12, a diaphragm 13, a collimator lens 14, a half mirror 15, a ring lens 16 and a two-dimensional photodetector 17 having sensitivity to a near infrared range. A part of reflection light of the light which converged at the fundus Ef by the projection optical system 100 (hereinafter, referred to as fundus reflection light) passes through the half mirror 10. The light which passed through the half mirror 10 passes through the objective lens 9, and a part thereof passes through the half mirror 8. The light which passed through the half mirror 8 is reflected by a peripheral plane of the hole of the hole mirror 7, passes through the relay lens 11 and is reflected by the total reflection mirror 12 to converge at a convergent point B on the optical axis L on an aperture plane of the diaphragm 13, and is made into parallel light by the collimator lens 14, and a part thereof is reflected by the half mirror 15. The light which was reflected by the half mirror 15 passes through the ring lens 16 to converge on a photo-receiving surface of the photodetector 17.

Incidentally, the Convergent point A by the condenser lens 4 and the convergent point B being an anterior focal point of the collimator lens 14 are conjugate with the fundus Ef via the objective lens 9 and the relay lenses 5 and 11. In addition, the condenser lens 4, the diaphragm 13, the collimator lens 14, the half mirror 15, the ring lens 16, and the photodetector 17 are arranged on a stage 18 movable in a direction of the optical axis L (the arrow D direction) by a driving unit (driving means) 63.

In addition, the ring lens 16 is arranged at a posterior focal point of the collimator lens 14 and is conjugate with a pupil Ep of the eye E regardless of a travel position of the stage 18. In addition, the photo-receiving surface of the photodetector 17 is arranged at a posterior focal point of the ring lens 16 and is conjugate with the fundus Ef regardless of the travel position of the stage 18. Incidentally, the ring lens 16 is made of a transparent plate on which a cylindrical lens is formed in a ring shape, and a light shielding coating is applied to a part other than the ring-shaped lens part. When the parallel light enters the ring lens 16, a ring image of approximately the same size as the ring lens 16 converges (is formed) at a focal point of the ring lens 16 (i.e., on a photo-receiving surface of the photodetector 17).

<Projection Optical System 300 for Eye Depth Information Obtainment>

The projection optical system 300 includes the light source 1, the collimator lens 2 and the half mirror 3 which are shared with the projection optical system 100, a total reflection mirror 19, a half mirror 20, a condenser lens 21 and a total reflection mirror 22, and the halt mirror 8, the objective lens 9 and the half mirror 10 which are shared with the projection optical system 100. The light which was emitted from the light source 1 and reflected by the half mirror 3 is reflected by the total reflection mirror 19, and a part thereof passes through the half mirror 20. The light which passed through the half mirror 20 converges at a convergent point C on the optical axis L by the condenser lens 21 and is reflected by the total reflection mirror 22, and a part thereof is reflected by the half mirror 8. The light which was reflected by the half mirror 8 passes through the objective lens 9, and a part thereof passes through the half mirror 10. The light which passed through the half mirror 10 converges in the vicinity of a cornea Ec of the eye E.

<Interference/Spectral/Photo-Receiving Optical System 400 for Eye Depth Information Obtainment>

The photo-receiving optical system 400 includes an optical system which photo receives the fundus reflection light and an optical system which photo-receives reflection light from the vicinity of the cornea Ec (hereinafter, corneal reflection light).

The fundus reflection light photo-receiving optical system includes the half mirror 10, the objective lens 9, the half mirror 8, the hole mirror 7, the relay lens 11, the total reflection mirror 12, the diaphragm 13, the collimator lens 14 and the half mirror 15 which are shared with the photo-receiving optical system 200, and a half mirror 26, a total reflection mirror 27, a condenser lens 28, an expander lens 29, a grating mirror (diffraction grating) 30, a condenser lens 31, a cylindrical lens 32, and a one-dimensional photodetector (line sensor) 33 having sensitivity to the near infrared range. The fundus reflection light by the projection optical system 100 passes through the respective optical members shared with the photo-receiving optical system 200, and a part thereof passes through the half mirror 15. A part of the light which passed through the half mirror 15 passes through the half mirror 26. The light which passed through the half mirror 26 is reflected by the total reflection mirror 27 to converge by the condenser lens 28, and has its light bundle diameter enlarged by the expander lens 29 to be dispersed into frequency components by the grating mirror 30. The dispersed light passes through the condenser lens 31 and the cylindrical lens 32 to converge on a photo-receiving surface of the photodetector 33. Incidentally, the light bundle diameter after the passage through the expander lens 29, grid intervals and an angle of incidence for the grating mirror 30, the condenser lens 28, and the photodetector 33 are optimized in consideration of a measurement region in an optical axis direction (a region in which depth information is obtained) and a resolution of the eye E.

The corneal reflection light photo-receiving optical system includes the half mirror 10, the objective lens 9 and the half mirror 8 which are shared with the fundus reflection light photo-receiving optical system (and the projection optical system 300), the total reflection mirror 22, the condenser lens 21 and the half mirror 20 which are shared with the projection optical system 300, a prism 23, a total reflection mirror 24 and a total reflection mirror 25, and the half mirror 26, the total reflection mirror 27, the condenser lens 28, the expander lens 29, the grating mirror 30, the condenser lens 31, the cylindrical lens 32 and the photodetector 33 which are shared with the fundus reflection light photo-receiving optical system. The prism 23 is arranged to be movable in the arrow H direction, which is moved by a driving unit (driving means) 64, whereby an optical path length of the light which passes through the prism 23 (the corneal reflection light in this embodiment) can be changed. A part of the corneal reflection light by the projection optical system 300 passes through the half mirror 10. The light which passed through the half mirror 10 passes through the objective lens 9, and a part thereof is reflected by the half mirror 8. The light which was reflected by the half mirror 8 is reflected by the total reflection mirror 22 and passes through the condenser lens 21, and apart thereof is reflected by the half mirror 20. The light which was reflected by the half mirror 20 is reflected by the prism 23 and the total reflection mirrors 24 and 25, and a part thereof is reflected by the half mirror 26. The light which was reflected by the half mirror 26 is made coaxial to be synthesized with the fundus reflection light (made to be interference light), and is dispersed into frequency components to converge on the photo-receiving surface of the photodetector 33, as in the case of the fundus reflection light.

Incidentally, the grating mirror 30, the condenser lens 31, the cylindrical lens 32, and the photodetector 33 constitute a spectrometer part. In addition, the photo-receiving surface of the photodetector 33 is conjugate with the fundus Ef and the cornea Ec. The cylindrical lens 32 acts to enlarge the light bundle diameter in a width direction of the photodetector 33 and is used to have the light converge on the photo-receiving surface regardless of a placement error of the photodetector 33.

<Reference-Light Forming Optical System 500>

The reference-light forming optical system 500 includes the light source 1, the collimator lens 2, the half mirror 3, the total reflection mirror 19 and the half mirror 20 which are shared with the projection optical system 300, and a total reflection mirror 34, a total reflection mirror 35, and a reference mirror 36 to be a reference surface. Besides, an optical path length from the reference mirror 36 (the reference surface) to the photodetector 33 is made to approximately correspond with an optical path length from a convergent position on the anterior segment (the vicinity of the cornea Ec) by the projection optical system 200 to the photodetector 33. In other words, in the optical system consistent with the present preferred embodiment, an optical path length from the convergent position on the anterior segment to the half mirror 20 and an optical path length from the reference mirror 36 to the half mirror 20 correspond approximately with each other On an optical path between the half mirror 20 and the total reflection mirror 34, an interception plate (shutter) 52 is arranged insertable and removable, which is inserted in and removed from the optical path by a driving unit (driving means) 67. Besides, a position in which the interception plate 52 is arranged is not limited to the above-described position, and it is essential only to arrange the interception plate 52 on an optical path which is singly used for the projection optical system 500 and not shared with the other optical systems described above.

The light which was emitted from the light source 1 and reflected by the half mirror 3 is reflected by the total reflection mirror 19, and a part thereof is reflected by the half mirror 20. The light which was reflected by the half mirror 20 is reflected by the total reflection mirrors 34 and 35, and further reflected by the reference surface of the reference mirror 36. The light which was reflected by the reference mirror 36 is reflected again by the total reflection mirrors 35 and 34, and a part thereof passes through the half mirror 20. The light which passed through the half mirror 20 is made coaxial to be synthesized with the corneal reflection light (made to be interference light), and reflected by the prism 23 and the total reflection mirrors 24 and 25, and a part thereof is reflected by the half mirror 26 to be dispersed into frequency components to converge on the photo-receiving surface of the photodetector 33, as in the case of the corneal reflection light.

<Fixation Target Presenting Optical System and Observation Optical System>

The fixation target presenting optical system includes a light source 37 such as a visible light emitting diode (LED), a target plate 38 on which a predetermined target is formed, a relay lens 39, a dichroic mirror 40 which transmits visible light and reflects the infrared light, an objective lens 41, and the half mirror 10. Light emitted from the light source 37 illuminates the target plate 38, and the light which passed through the target plate 38 passes through the relay lens 39, the dichroic mirror 40 and the objective lens 41, and a part thereof is reflected by the half mirror 10 to form an image on the fundus Ef. Incidentally, when the present apparatus is aligned to have a predetermined positional relationship with the eye E, the target plate 38 is conjugate with the fundus Ef. In addition, the light source 37 and the target plate 38 are arranged to be movable in an optical axis direction (the arrow F direction), which are moved by a driving unit (driving means) 65, allowing fixation of the eye E, fogging on the eye E at the time of eye refractive power measurement.

The observation optical system includes the half mirror 10, the objective lens 41, the dichroic mirror 40, an image forming lens 42, and a two-dimensional photodetector 43 having sensitivity to the infrared range. Besides, a photo-receiving surface of the photodetector 43 is conjugate with the pupil Ep. The anterior segment of the eye E is illuminated by a light source 44 such as an infrared LED, and reflection light therefrom is reflected by the half mirror 10, passes through the objective lens 41, and is reflected by the dichroic mirror 40 to form an image on the photodetector 43 by the image forming lens 42.

A control part 60 which controls the present apparatus is connected with the photodetector 17, the photodetector 33, the photodetector 43, a monitor 61, a calculation/processing part 62, the driving units 63 to 67, a storage part 68, a switch unit 69 and the like. The driving units 63 to 67 include pulse motors and the like, and respective driving amounts thereof are made detectable. The calculation/processing part 62 is used to perform calculation for obtaining ocular information such as eye refractive power and an axial length of the eye E and to form a tomographic image of the eye E based on information obtained by the respective photodetectors, the respective driving units, and the like. Calculated measurement (obtainment) values are stored in the storage part 68. Various kinds of switches such as a measurement starting switch and a measurement mode changing switch are provided to the switch unit 69.

Hereinafter, described will be operation of the apparatus as stated above. Besides, the description below will be given separately to a case where the eye refractive power and the axial length of the eye E are measured and to a case where the depth information of the anterior segment of the eye E is obtained.

<Eye Refractive Power Measurement and Axial Length Measurement>

When a signal for setting a measurement mode for eye refractive power and axial length is input from the measurement mode changing switch, the control part 60 drives the driving units 66 and 67 to remove the interception plate 51 from the optical path and insert the interception plate 52 in the optical path, bringing the optical arrangement to a state shown in FIG. 1.

When the apparatus is aligned to have a predetermined positional relationship with the eye E, the target by the fixation target presenting optical system is presented to the eye E. Besides, in this embodiment, a photo-receiving surface of the photodetector 43 and the pupil Ep are made conjugate.

When a trigger signal is input from the measurement starting switch, the control part 60 drives the driving unit 65 to move the light source 37 and the target plate 38, and fog the eye E so as to eliminate its accommodation. In addition, the control part 60 controls the light source 1 to emit light. The light which was emitted from the light source 1 is split by the half mirror 3 to converge at the fundus Ef and the vicinity of the cornea Ec via the projection optical system 100 and the projection optical system 300. The reflection light from the fundus Ef is photo-received on the photodetector 17 via the photo-receiving optical system 200.

Figure 3A:
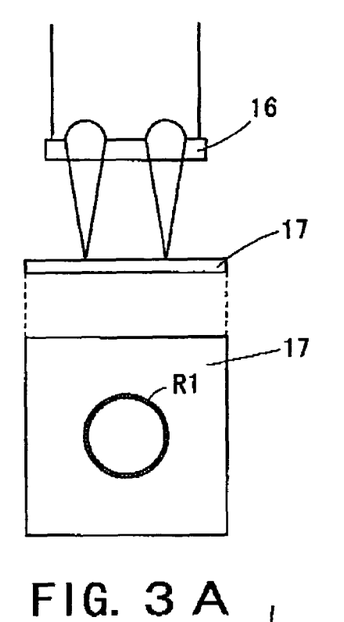
FIGS. 3A to 3C are views showing a convergence state of light which passed through a ring lens.
Figure 3B:
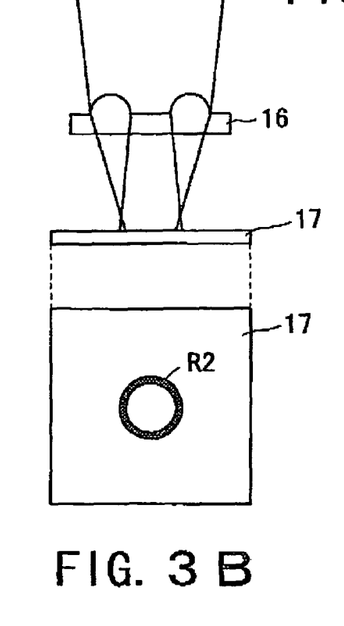
Figure 3C:
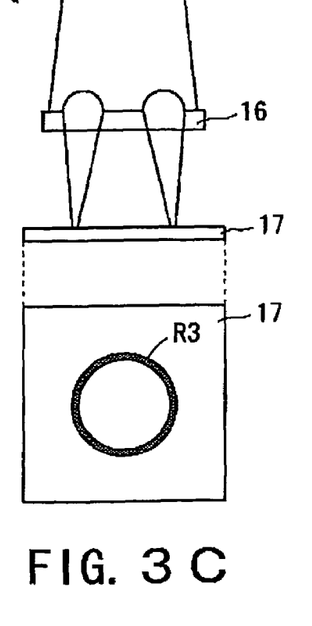

FIGS. 3A to 3C are views showing a photo-receiving state of the fundus reflection light which passed through the ring lens 16 and was photo-received on the photodetector 17. For example, if the eye E is emmetropia, the fundus reflection light which passed through the collimator lens 14 becomes parallel light to pass through the ring lens 16. A ring image R1 on the photodetector 17 in this case is approximately the same in size as the ring lens 16 (see FIG. 3A). If the eye E is myopia, the fundus reflection light which passed through the collimator lens 14 becomes convergent light to pass through the ring lens 16. A ring image R2 on the photodetector 17 in this case becomes thicker and smaller than the ring image R1 (see FIG. 3B). If the eye E is hyperopia, the fundus reflection light which passed through the collimator lens 14 becomes divergent light to pass through the ring lens 16. A ring image R3 on the photodetector 17 in this case becomes thicker and larger than the ring image R1 (see FIG. 3C).

The calculation/processing part 62 obtains the eye refractive power of the eye E based on an amount of change of an actual photo-receiving state on the photodetector 17 with respect to a photo-receiving state on the photodetector 17 when the eye E is emmetropia. In addition, based on the obtained eye refractive power or the photo-receiving state on the photodetector 17, the calculation/processing part 62 obtains a position of the stage 18 with which the light projected onto the fundus Ef converges the most (focuses the best) at the fundus Ef. The calculation/processing part 62 transmits information on the obtained position of the stage 18 to the control part 60, and based on the positional information, the control part 60 drives the driving unit 63 to move the stage 18 and makes refractive power correction on the eye E. By making the refractive power correction on the eye E in this way, a convergence state of the light projected onto the fundus Ef can be corrected, allowing an interference signal with a favorable S/N ratio to be obtained (detected).

Incidentally, the eye refractive power of the eye E is obtained based on the photo-receiving state of the ring image on the photodetector 17 in this embodiment; however, the present invention is not limited thereto, and the eye refractive power of the eye E may be obtained also in consideration of a position of the stage 18 which is regarded as the best focusing position for making the light converge at the fundus Ef, and the photo-receiving state of the ring image at the time. In addition, it is also possible to use the information on the photo-receiving state of the ring image in calculating the positional information on the stage 18 for attaining the best focus, and then to obtain the eye refractive power of the eye E based on a travel amount of the stage 18 from a reference position. The obtained eye refractive power of the eye E is stored in the storage part 68 and displayed on the monitor 61.

Owing to the refractive power correction of the eye E by the movement of the stage 18, the light projected onto the fundus Ef can efficiently converges. The fundus reflection light (in this embodiment, the fundus reflection light is regarded as reference light) is photo-received on the photodetector 33 via the photo-receiving optical system 400. In addition, the corneal reflection light (in this embodiment, the corneal reflection light is regarded as object light) is also photo-received on the photodetector 33 via the photo-receiving optical system 400. The photodetector 33 photo-receives the respective reflection light dispersed in the frequency components and outputs the interference signal for each of the frequency components. The calculation/processing part 62 monitors the interference signals obtained by the photodetector 33.

Meanwhile, the control part 60 drives the driving unit 64 to move the prism 23 from a reference position indicated by solid lines (the reference position shown here is a position with which an optical path length of the corneal reflection light is made shortest), changing the optical path length of the corneal reflection light. Incidentally, the prism 23 is given reciprocating motions several times to over ten times a second during the axial length measurement in this embodiment; however, the present invention is not limited thereto, and the prism 23 may be moved simply in one direction.

As this embodiment employs light with short coherence length for the object light and the reference light, when an optical path length of the object light and an optical path length of the reference light become equal, strength of a signal of interference light obtained by synthesizing both of the light becomes maximum. Incidentally, the object light photo-received on the photodetector 33 includes reflection light from phase objects such as a rear surface of the cornea Ec, an anterior surface of a crystalline lens El and a posterior surface of the crystalline lens El, in addition to the reflection light from a front surface of the cornea EC. Accordingly, the interference signals outputted from the photodetector 33 include interference between the object light including such reflection light from the phase objects and the fundus reflection light (reference light) as a function of frequency.

The calculation/processing part 62 performs Fourier transform to analyze the interference signals outputted from the photodetector 33. Since the interference light includes the reflection light from the respective phase objects of the eye E (e.g., the front/rear surfaces of the cornea Ec, the anterior/posterior surfaces of the crystalline lens El, and the fundus Ef), Fourier transform on the interference signals enables obtaining depth information of the respective phase objects of the eye E regarding the fundus Ef as a reference surface. The calculation/processing part 62 obtains an axial length of the eye E based on positional information on the front surface of the cornea Ec with reference to the position of the prism 23, which was obtained by the calculation, and a travel amount of the prism 23 from the reference position (alternatively, a driving amount of the driving unit 64). Besides, concerning the reference position (initial position) of the prism 23, by performing calibration using a model eye or the like of which the axial length is previously known, the reference position of the prism 23 is made to correspond to a predetermined axial length.

The obtained axial length is stored in the storage part 68 and displayed on the monitor 61. Incidentally, the optical path length of the object light and that of the reference light are made equal by changing the optical path length of the corneal reflection light (object light) in this embodiment; however, the present invention is not limited thereto, and an optical path length of the fundus reflection light (reference light) may be changed.

In addition, in a case where a more accurate axial length is to be obtained, an optical member for astigmatic correction constituted of a combination of a plurality of cylindrical lenses may be arranged at a conjugate position with the pupil Ep between the collimator lens 14 and the condenser lens 27, or at a conjugate position with the pupil Ep between the objective lens 9 and the hole mirror 7. For example, a Stokes' cross-cylinder constituted of a combination of two cylindrical lenses is used as the optical member for astigmatic correction. Since the ring image on the photodetector 17 becomes oval if the eye E has astigmatism, astigmatic power and an astigmatic axial angle can be obtained through analysis of the photo-receiving state of the ring image by the calculation/processing part 62. Based on the obtained astigmatic power and astigmatic axial angle of the eye E, the aforementioned optical member for astigmatic correction is arranged so as to cancel out an astigmatic component of the eye E. Owing to such configuration, even if the eye E has the astigmatic component, the fundus reflection light efficiently converges at the photodetector 33, whereby measurement accuracy can be enhanced.

<Anterior-Eye-Segment Depth Information Obtainment>

Figure 4:
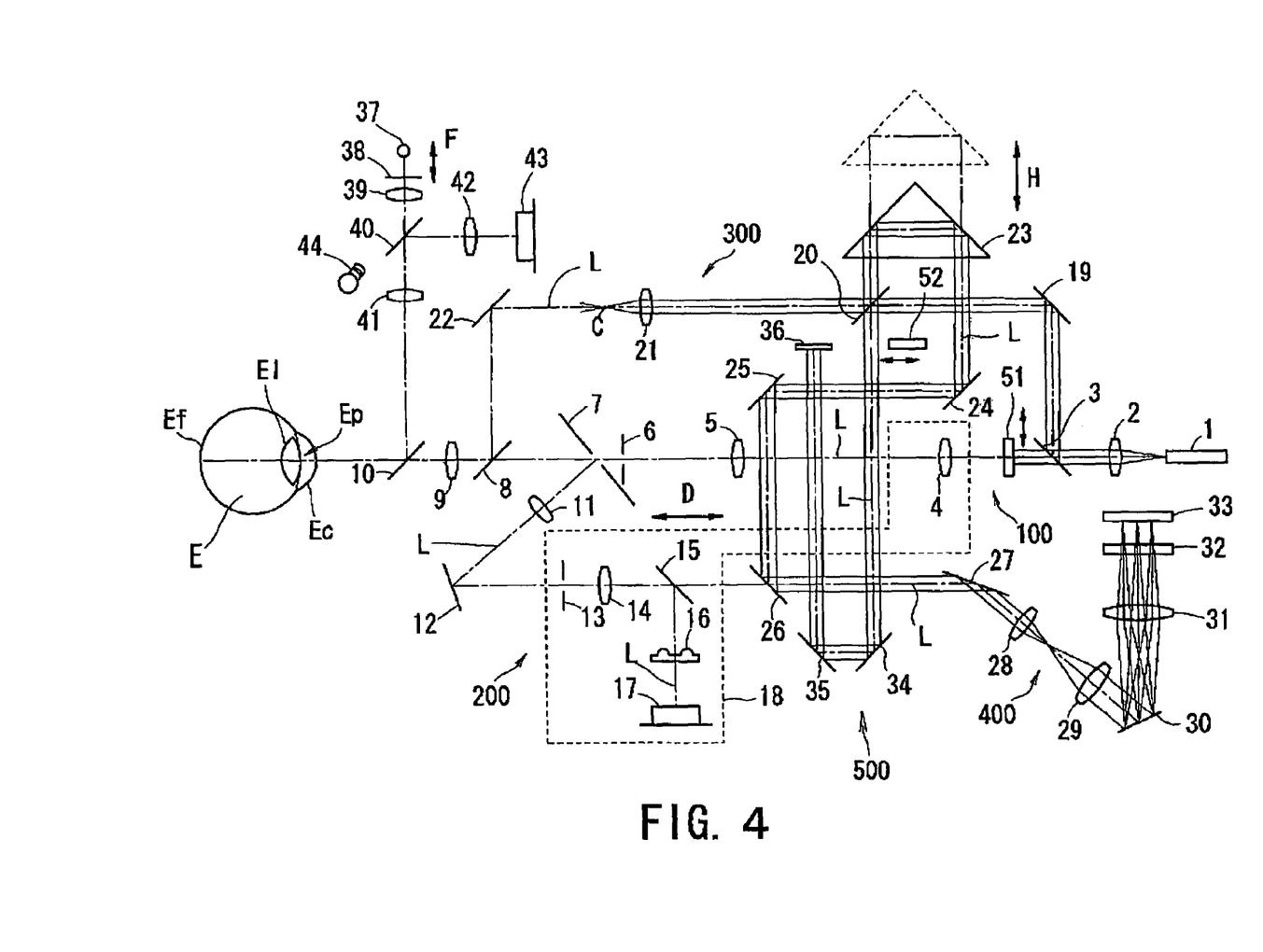
FIG. 4 is a view showing an optical arrangement of the optical system of FIG. 1 when obtaining depth information of an anterior segment of an eye.

When a signal for setting an obtainment mode for anterior-eye-segment depth information is input from the measurement mode changing switch, the control part 60 drives the driving units 66 and 67 to insert the interception plate 51 in the optical path and remove the interception plate 52 from the optical path, bringing the optical arrangement to a state shown in FIG. 4.

When the apparatus is aligned to have a predetermined positional relationship with the eye E, and a trigger signal is input from the measurement starting switch, the control part 60 controls the light source 1 to emit light. The light which was emitted from the light source 1 and reflected by the half mirror 3 is split by the half mirror 20. The light which passed through the halt mirror 20 converges at the vicinity of the cornea Ec via the projection optical system 300. The light which was reflected by the half mirror 20 is directed to the reference-light forming optical system 500.

The corneal reflection light (object light) is photo-received on the photodetector 33 via the photo-receiving optical system 400. On the other hand, the light which was directed to the reference-light forming optical system 500 (i.e., reference light) is reflected by the reference mirror 36 to be synthesized with the corneal reflection light by the half mirror 20, and photo-received on the photodetector 33 via the photo-receiving optical system 400. Incidentally, as described above, the optical path length from the convergent position in the vicinity of the cornea Ec to the half mirror 20 and the optical path length from the reference mirror 36 to the half mirror 20 correspond approximately with each other, so that the object light and the reference light interfere with each other. The photodetector 33 photo-receives the respective reflection light dispersed in the frequency components and outputs an interference signal for each of the frequency components. The calculation/processing part 62 monitors the interference signals outputted from the photodetector 33. Incidentally, in the obtainment mode for anterior-eye-segment depth information, it is configured that the object light and the reference light enter the prism 23 in a state being synthesized, so that the position of the prism 23 is not limited specifically.

The calculation/processing part 62 performs Fourier transform to analyze the interference signals outputted from the photodetector 33. Since the interference light includes the reflection light from the respective phase objects in the periphery of the anterior segment of the eye E (e.g., the front/rear surfaces of the cornea Ec and the anterior/posterior surfaces of the crystalline lens El), Fourier transform on the interference signals enables obtaining depth information of the respective phase objects such as the cornea Ec and the crystalline lens El. Based on the obtained depth information, the calculation/processing part 62 obtains depth information (here, dimensional information) of the anterior segment such as thickness of the cornea, thickness of the crystalline lens, depth of an anterior chamber and the like of the eye E. The obtained depth information of the anterior segment is stored in the storage part 68 and displayed on the monitor 61.

At the time of the anterior-eye-segment depth information obtainment, employing the fundus reflection light as reference light is apt to cause reflectance distribution because of influence of various phase objects of the fundus Ef, and there is a possibility that measurement results of high precision cannot be obtained. Accordingly, in this embodiment, the reference light by the reference-light forming optical system provided inside the apparatus is employed, allowing measurement results of high precision to be obtained.

Incidentally, the object light converges at the cornea Ec in this embodiment; however, the present invention is not limited thereto, and it is essential only that the reflection light from the phase objects of the eye E (the cornea Ec, the crystalline lens El and the like) is photo-received on the photodetector 33 in a state dispersed in the frequency components; for example, a convergent position of the object light may be in the vicinity of the cornea Ec, such as the pupil Ep.

Additionally, the grating mirror (diffraction grating) 30 is employed in this embodiment as a dispersing unit (dispersing means) for dispersing the synthetic light (interference light) of the object light and the reference light into the respective frequency components; however, the present invention is not limited thereto, and some other dispersing means such as a transmission grating prism and an acoustic optical element may be employed.

Further, it is configured that the ring image is formed on the photodetector 17 in order to obtain the eye refractive power of the eye E in this embodiment; however, the present invention is not limited thereto, and it is essential only to be configured such that the eye refractive power is obtained by detecting a state of change including positional change and shape change in the photo-received image formed on the photo-receiving surface without using interference; for example, it is essential only to be configured such that the fundus reflection light is divided into several dots via an optical member and made to converge at the photodetector, and based on a photo-receiving state of an image of the dots on the photodetector, the eye refractive power is obtained.

Incidentally, by further providing a scanning unit (scanning means) for scanning the light to be projected onto the eye E and by analyzing interference signals outputted from the photodetector 33 according to the principle of spectral interference, a tomographic image of the anterior segment of the eye E can be also obtained.

Figure 5:
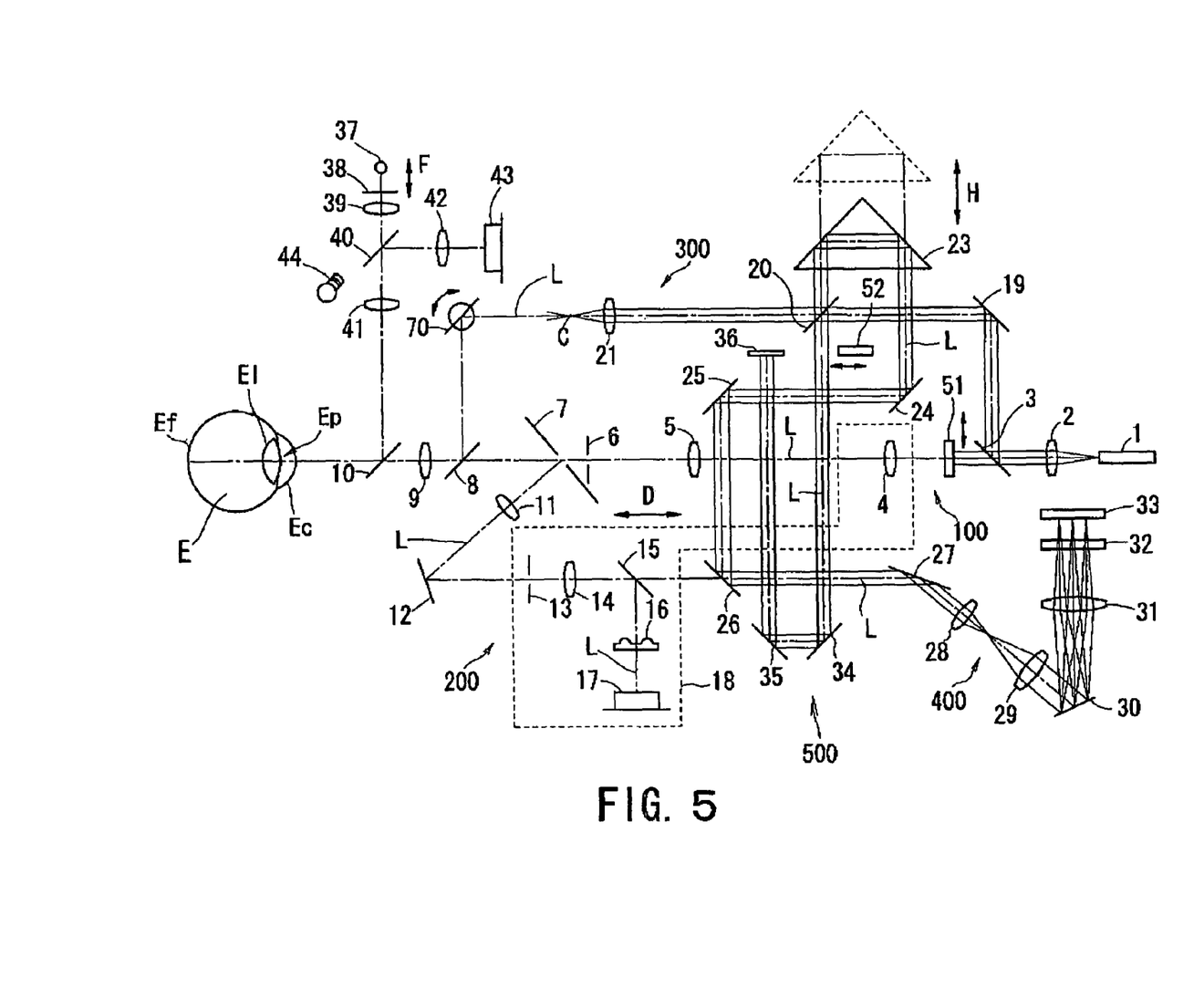
FIG. 5 is a view showing a schematic configuration of a modified example 1 of the optical system of the present apparatus.

FIG. 5 is a view showing a schematic configuration of a modified example 1 of the optical system of the present apparatus, in which the scanning unit which scans the light to be projected onto the eye E is provided.

A galvano mirror 70 being the scanning unit is capable of rotating (swinging) in a predetermined direction (in this embodiment, a direction in which the light is scanned up and down with respect to, the eye E). In addition, a reflection plane of the galvano mirror 70 is arranged at a focal point of the objective lens 9, and it is arranged such that a rotational angle is proportional to a height of incidence of the light to the anterior segment and an optical path length does not change. Besides, the optical arrangement at the time of obtaining the tomographic image of the anterior segment is a state such that the interception plate 51 is inserted in the optical path and the interception plate 52 is removed from the optical path.

Light which was emitted from the light source 1 to pass through the half mirror 20 converges in the vicinity of the cornea Ec. On the other hand, light which was emitted from the light source 1 to be reflected by the half mirror 20 is reflected by the reference mirror 36. Synthetic light of object light (reflection light from the phase objects of the anterior segment) and reference light (reflection light from the reference mirror 36) is dispersed into frequency components to be photo-received on the photo-detector 33. The calculation/processing part 62 performs Fourier transform on interference signals outputted from the photodetector 33, allowing depth information of the respective phase objects such as the cornea Ec and the crystalline lens El of the eye E to be obtained.

Figure 6:
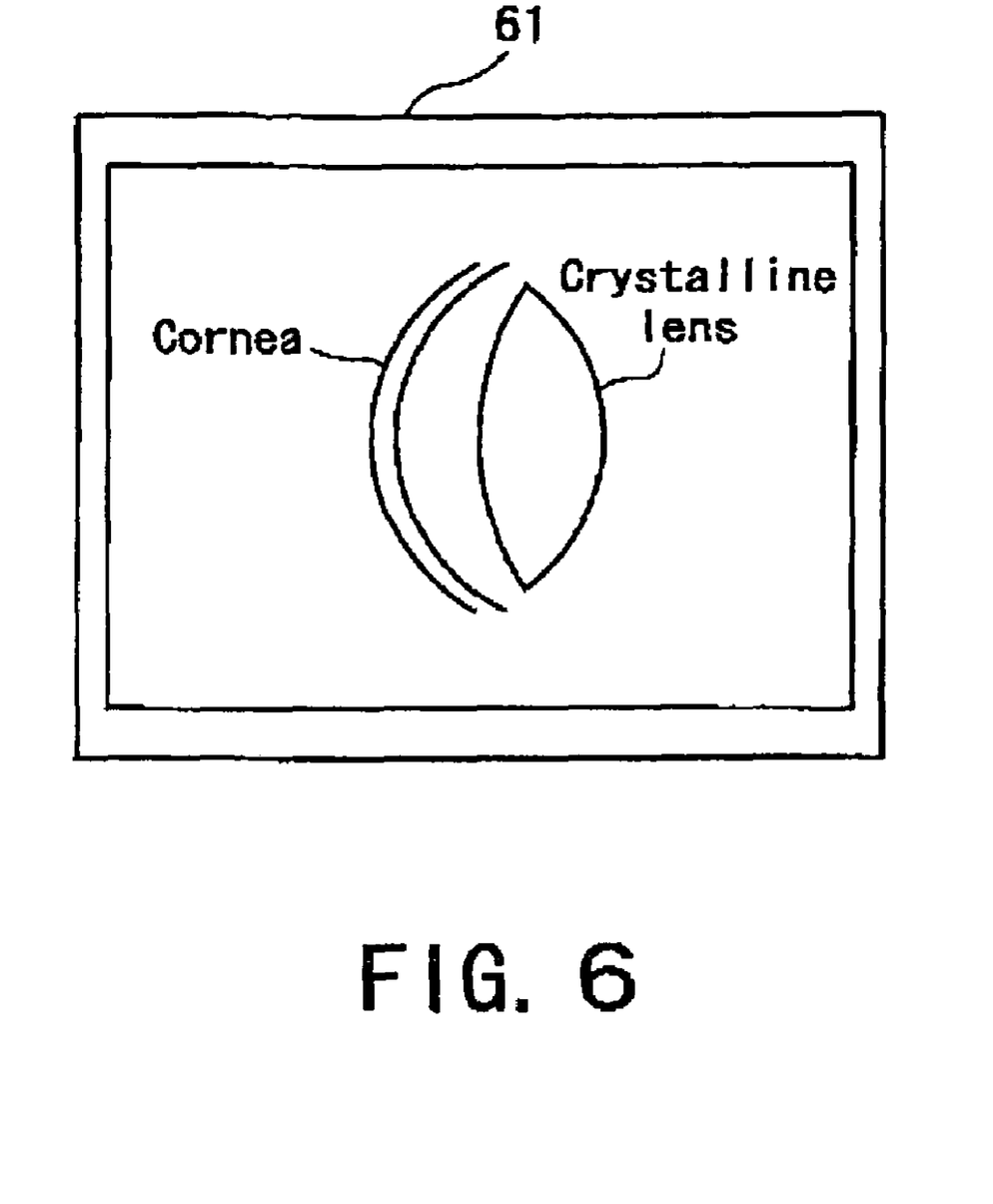
FIG. 6 is a view showing a tomographic image of the anterior segment displayed on a monitor.

Incidentally, the object light is scanned by the galvano mirror 70 in the predetermined direction with respect to the eye E. Accordingly, the interference signals outputted from the photodetector 33 include information on the respective reflection light from the phase objects of the eye E obtained by scanning the light. By accumulating and adding the depth information of the phase objects obtained by performing Fourier transform on the interference signals, the calculation/processing part 62 can obtain a tomographic image of the anterior segment optically sectioned by scanning. The obtained tomographic image of the anterior segment is displayed on the monitor 61 as shown in FIG. 6. Besides, the dimensional information on the anterior segment is also displayed on the monitor 61.

Figure 7:
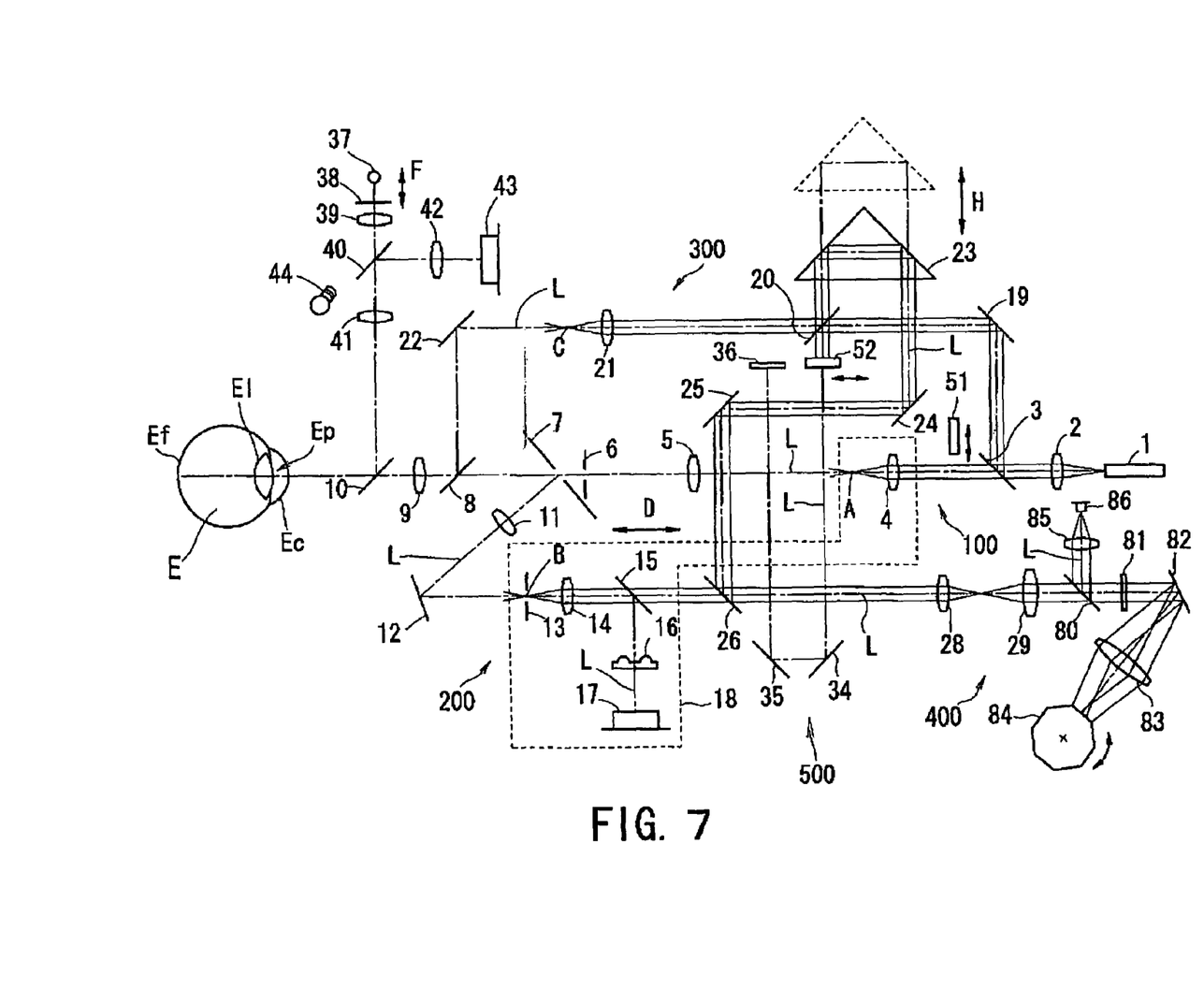
FIG. 7 is a view showing a schematic configuration of a modified example 2 of the optical system of the present apparatus.

In the embodiment described above, the one-dimensional photodetector (line sensor) is employed in the spectrometer part; however, the present invention is not limited thereto. Hereinafter, description is given to a modified example 2 where a single photodetector is employed in the spectrometer part, which is shown in FIG. 7. Besides, an optical system shown in FIG. 7 is the same as that in FIG. 1 except the spectrometer part, so that the description is given only to the spectrometer part hereinafter.

As illustrated, the spectrometer part includes a polarization beam splitter 80, a quarter wavelength plate 81, a grating mirror (diffraction grating) 82, a lens group 83, a polygon mirror 84, a condenser lens 85, a single photodetector 86 such as a photodiode. The polarization beam splitter 80 has properties of transmitting light of a P wave and reflecting light of an S wave. The lens group 83, which consists of a plurality of lenses and is arranged between the grating mirror 82 and the polygon mirror 84, is designed so that principal rays of light in respective frequency components intersect at one point while the light in the respective frequency components which was reflected by the grating mirror 82 and entered as parallel light is made parallel even after refraction. The polygon mirror 84 is arranged so that a rotation axis thereof corresponds with the above-described point where the principal rays of the light in the respective frequency components intersect. The single photodetector 86 has photo-receiving sensitivity to the near infrared range considerably higher than the one-dimensional photodetector does The synthetic light (interference light) of the object light and the reference light converges by the condenser lens 28 to have its light bundle diameter enlarged by the expander lens 29, and only the light of the P wave is transmitted by the polarization beam splitter 80. The light which was transmitted by the polarization beam splitter 80 passes through the quarter wavelength plate 81 to be dispersed into the respective frequency components by the grating mirror 82. The dispersed light passes through the lens group 83 to be reflected by the polygon mirror 84. The polygon mirror 84 is rotated at a predetermined speed, and depending on an angle of a reflection plane thereof, only the light of a specific frequency goes back the optical path it has come. The light which was reflected by the polygon mirror 84 passes through the lens group 83, is reflected by the grating mirror 82, passes through the quarter wavelength plate 81 to become the light of the S wave, and is reflected by the polarization beam splitter 80. The light which was reflected by the polarization beam splitter 80 converges on a photo-receiving surface of the photodetector 86 by the condenser lens 85. Consequently, when the polygon mirror 84 is rotated successively, the photodetector 86 is to obtain interference signals of the respective frequencies (respective wavelength) successively as a function of time. The calculation/processing part 62 performs Fourier transform to analyze the interference signals outputted from the photodetector 86 and obtains depth information of the respective phase objects of the eye E. By employing the single photodetector as mentioned above, the photo-receiving sensitivity can be increased.

Incidentally, the polygon mirror 84 is employed as means for making the light dispersed in the respective frequencies to be photo-received on the photodetector 86 in chronological order; however, the present invention is not limited thereto, and it is essential only to employ a rotatable mirror such as a galvano mirror. Additionally, it is essential only to employ means with which the light dispersed in the respective frequencies can be time-divisionally photo-received on the photodetector 86 successively.

In addition, in this embodiment, the light which was reflected by the polygon mirror 84 is made to be reflected toward the photodetector 86 by the polarization beam splitter 80; however, the present invention is not limited thereto, and it is essential only to be configured such that the light which was reflected by the polygon mirror 84 is prevented from reentering the eye E, the reference mirror, the light source and the like. For example, in the optical arrangement shown in FIG. 7, a half mirror may be arranged instead of the polarization beam splitter 80 and a polarization beam splitter may be arranged in such a predetermined position on the same optical path that the polarization beam splitter does not hinder the measurement.

As described above, according to the ophthalmic apparatus consistent with the present embodiment, various ocular information can be effectively obtained with one apparatus. Incidentally, in the above-described axial length measurement, the fundus reflection light regarded as the reference light and the corneal reflection light regarded as the object light are made to interfere with each other to be analyzed according to the principle of spectral interference, so that both of the reference light and the object light change to the same degree even if the position of the examinee's eye is somewhat deviated with respect to the apparatus; therefore, the apparatus has an advantage of being unsusceptible to alignment deviation and focus deviation. In addition, in the anterior-eye-segment depth information obtainment, the reference light is formed inside the apparatus and made to interfere with the object light, allowing a noise component to be minimized; therefore, the anterior-eye-segment depth information of high precision can be obtained. In addition, it goes without saying that the configuration of the spectrometer part in FIG. 7 is applicable not only to an ophthalmic apparatus, but also to other measurement apparatuses which obtain depth information of an object to be examined, Incidentally, in the description above, the configuration for obtaining the axial length and the anterior-eye segment depth information has been mentioned as configuration for obtaining ocular information; however, the present invention is not limited thereto.

Hereinafter, description is given to configuration for obtaining the axial length and depth information of the fundus Ef.

Figure 8:
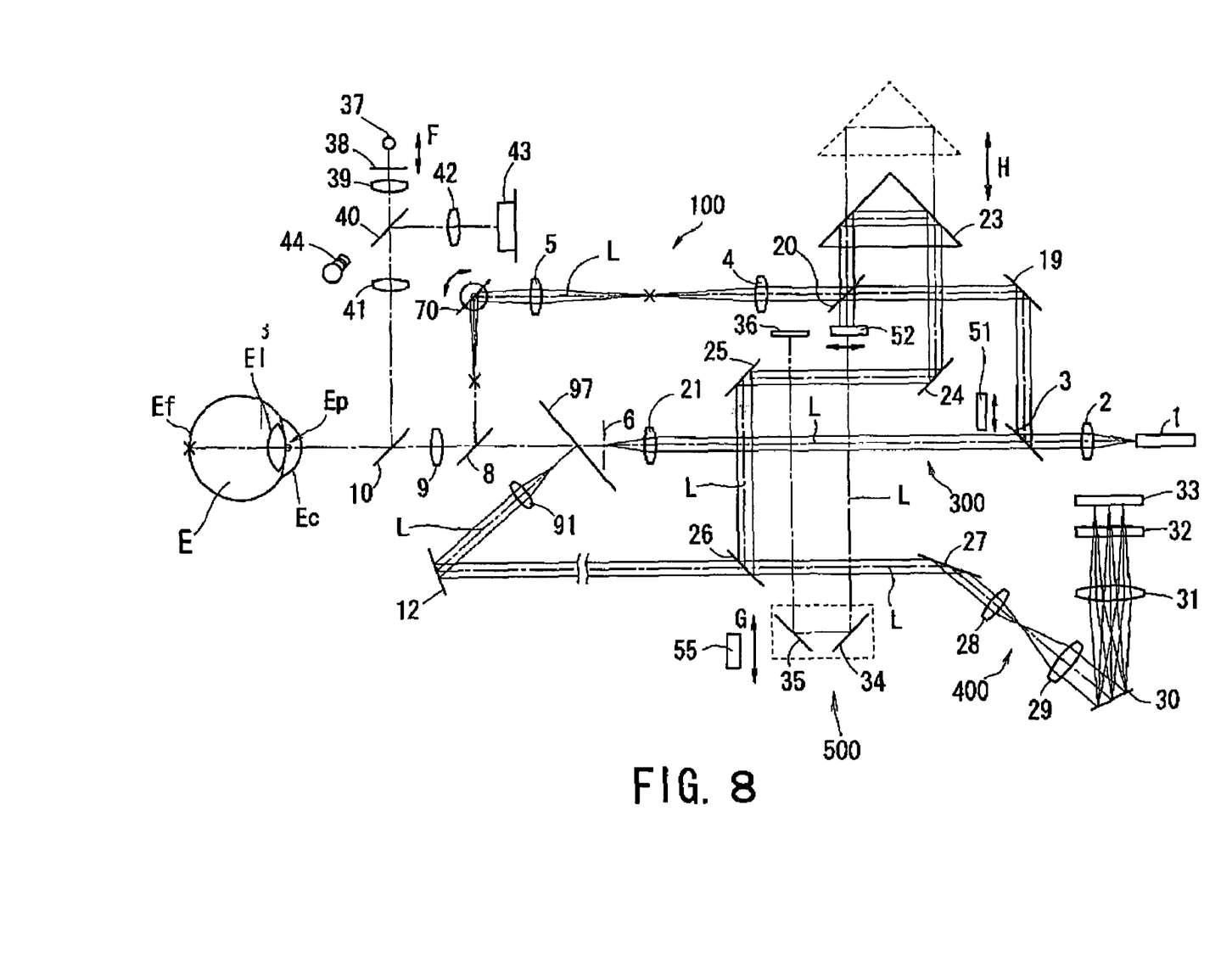
FIG. 8 is a view showing a schematic configuration of a modified example 3 of the optical system of the present apparatus.

FIG. 8 is a view showing a schematic configuration of a modified example 3 of the optical system of the present apparatus. In this configuration, the projection optical system 100 is arranged on a reflection side of the half mirror 3, and the projection optical system 300 is arranged on a transmission side of the half mirror 3. Besides, an optical arrangement at the time of obtaining the axial length is such that the interception plate 51 is removed from the optical path and the interception plate 52 is inserted in the optical path. The reflection plane of the galvano mirror 70 is conjugate with the pupil Ep. In addition, a half mirror 97 is arranged instead of the hole mirror 7. In addition, an unillustrated alternative path for adjusting a difference between the optical path length of the corneal reflection light and the optical path length of the fundus reflection light is provided between the total reflection mirror 12 and the half mirror 26.

The fundus reflection light which was reflected by the half mirror 20 via the half mirror 10, the objective lens 9, the half mirror 8, the galvano mirror 70, the relay lens 5 and the condenser lens 4 is reflected by the prism 23 and the total reflection mirrors 24 and 25, and a part thereof is reflected by the half mirror 26. In addition, the cornea reflection light which was reflected by the half mirror 97 via the half mirror 10, the objective lens 9 and the half mirror 8 passes through the collimator lens 91 and is reflected by the total reflection mirror 12, and a part thereof passes through the half mirror 26.

When obtaining the axial length, the control part 60 controls to move the prism 23 to gradually change an optical path length of the fundus reflection light, and based on interference signals outputted from the photodetector 33, a position of the prism 23 when strength of a signal of synthetic light (interference light) of the fundus reflection light (object light) and the corneal reflection light (reference light) becomes maximum is detected. Then, the calculation/processing part 62 obtains the axial length of the eye E based on positional information on a posterior surface of a retina with reference to the position of the prism 23 obtained through calculation and a travel amount of the prism 23 from the reference position (alternatively, a driving amount of the driving means 54).

Figure 9:
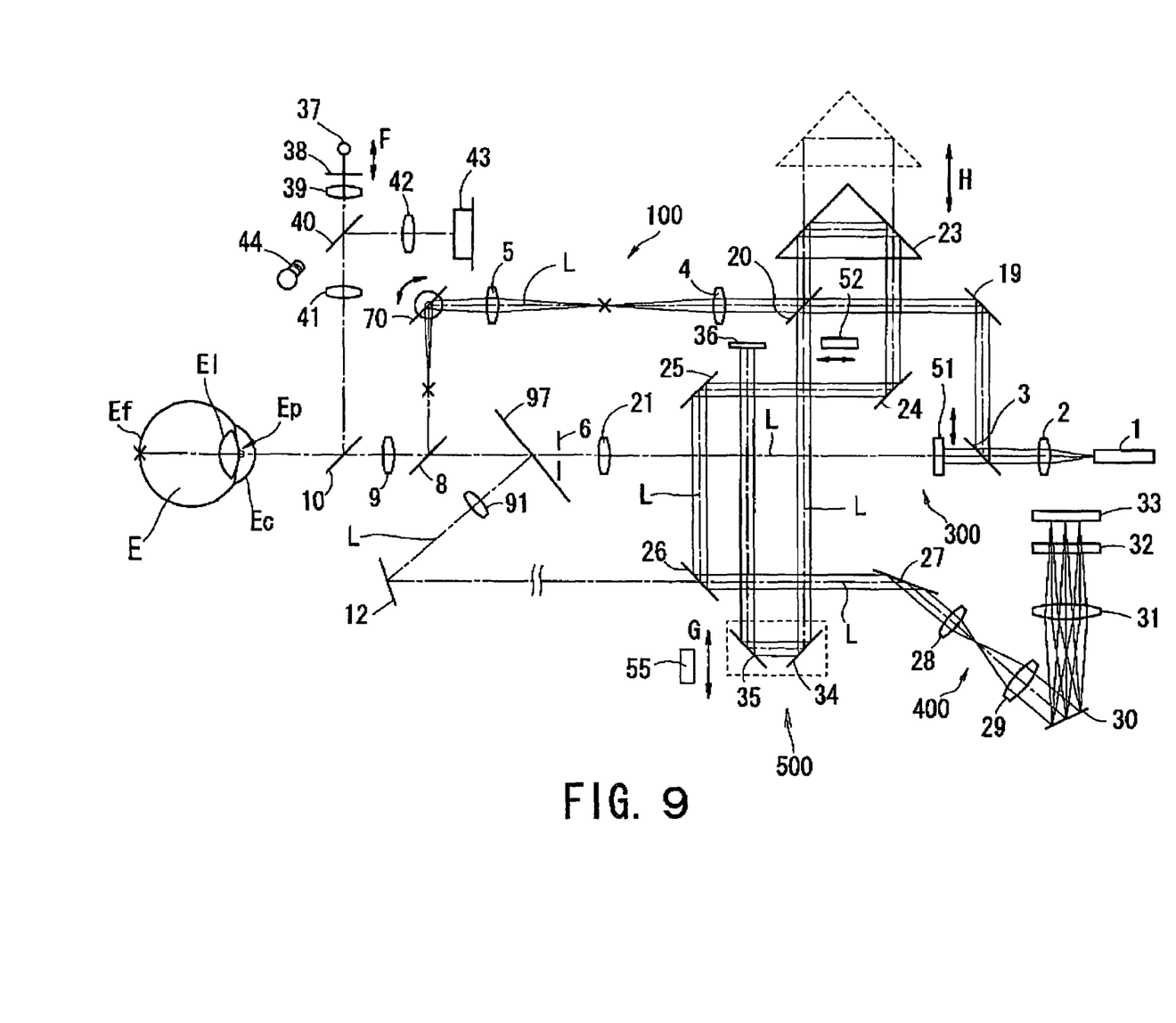
FIG. 9 is a view showing an optical arrangement of the optical system of FIG. 8 when obtaining depth information of a fundus.

Meanwhile, an optical arrangement at the time of obtaining the depth information of the fundus Ef is such that the interception plate 51 is inserted in the optical path and the interception plate 52 is removed from the optical path (a state as shown in FIG. 9). In this case, instead of the corneal reflection light by the projection optical system 30, reference light by the reference-light forming optical system 500 is directed to the photo-receiving optical system 400. In other words, a part of the light which was emitted from the light source 1 and reflected by the half mirror 3 is reflected by the half mirror 20 and the reference mirror 36, and a part thereof passes through the half mirror 20 to be reflected by the prism 23, and a part thereof is reflected by the half mirror 26, and then the light is made coaxial to be synthesized with the fundus reflection light (the object light) Besides, the total reflection mirrors 34 and 35 are arranged to be movable in the arrow G direction and moved by a driving unit (driving means) 55, whereby an optical path length of the reference light can be changed without changing the optical path length of the fundus reflection light.

Here, the control part 60 controls to move the total reflection mirrors 34 and 35 integrally, making the optical path length of the fundus measurement light which varies with the axial length and the optical path length of the reference light approximately equal, whereby the fundus reflection light and the reference light are synthesized to interfere with each other.

In this case, as the interference light includes reflection light from the phase objects in the periphery of the fundus Ef (e.g., anterior/posterior surfaces of the retina), the calculation/processing part 62 can obtain depth information of the respective phase objects such as the retina by performing Fourier transform on interference signals outputted from the photodetector 33. Based on the depth information, the calculation/processing part 62 obtains the depth information (here, dimensional information) of the fundus Ef.

In addition, in the case of obtaining a tomographic image of the fundus Ef, the control part 60 drives the galvano mirror 70 to scan the light which is to converge at the fundus Ef in a predetermined direction with respect to the fundus Ef. Thereafter, by accumulating and adding the depth information of the phase objects obtained by performing Fourier transform on the interference signals outputted from the photodetector 33, the calculation/processing part 62 can obtain the tomographic image of the fundus Ef which was optically sectioned by scanning.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for obtaining ocular information on an examinee's eye without contacting the eye, the apparatus comprising:
    a first projection optical system comprising:
        a light source which emits light with short coherence length; and
        an optical member which disperses the light emitted from the light source,
    which makes a first portion of the dispersed light converge as a first light at a fundus of the eye;
    a second projection optical system which makes a second portion of the dispersed light converge as a second light at an anterior segment of the eye;
    a photo-receiving optical system comprising:
        an optical path length changing unit which changes at least one of an optical path length of the first light and an optical path length of the second light in order to synthesize the first light reflected from the fundus and the second light reflected from the anterior segment into interference light,
    and where the photo-receiving optical system disperses the interference light into frequency components, and photo-receives the dispersed interference light with a first photodetector; and
    a calculation part which obtains an axial length of the eye as ocular information based on a result obtained by analyzing an output signal from the first photodetector by means of Fourier transform and an amount of change of at least one of the optical path length of the first light and the optical path length of the second light.

2. The ophthalmic apparatus according to claim 1, further comprising:
    a reference-light forming optical system for forming reference light, the system provided inside the apparatus;
    a light directing unit which directs any one of the first light and the reference light to the photo-receiving optical system; and
    a control part which drives and controls the light directing unit to direct the first light to the photo-receiving optical system to be synthesized and interfere with the second light when obtaining the axial length, and to direct the reference light to the photo-receiving optical system to be synthesized and interfere with the second light when obtaining the depth information of the anterior segment.

3. The ophthalmic apparatus according to claim 2, wherein an optical path length from a reference surface of the reference-light forming optical system to a photo-receiving surface of the first photodetector is determined to approximately correspond with an optical path length from a convergent position of the second light on the anterior segment to the photo-receiving surface of the first photodetector.

4. The ophthalmic apparatus according to claim 2, wherein
the second projection optical system includes a scanning unit which scans the second light, and
the calculation part obtains a tomographic image of the anterior segment.

5. The ophthalmic apparatus according to claim 1 further comprising:
a reference-light forming optical system which forms reference light, the system provided inside the apparatus;
a light directing unit which directs any one of the second light and the reference light to the photo-receiving optical system; and
a control part which drives and controls the light directing unit to direct the second light to the photo-receiving optical system to be synthesized and interfere with the first light when obtaining the axial length, and to direct the reference light to the photo-receiving optical system to be synthesized and interfere with the first light when obtaining the depth information of the fundus.

6. The ophthalmic apparatus according to claim 5, wherein an optical path length from a reference surface of the reference-light forming optical system to a photo-receiving surface of the first photodetector is determined to approximately correspond with an optical path length from a convergent position of the first light on the fundus to the photo-receiving surface of the first photodetector.

7. The ophthalmic apparatus according to claim 5, wherein
the first projection optical system includes a scanning unit which scans the first light, and
the calculation part obtains a tomographic image of the fundus.

8. The ophthalmic apparatus according to claim 1, wherein the photo-receiving optical system includes:
a dispersing unit which disperses the interference light into the frequency components; and
a time-division unit which divides the dispersed light in chronological order, and
the first photodetector is a single photodetector which photo-receives the divided light.

9. The ophthalmic apparatus according to claim 8, wherein the time-division unit is a movable mirror which divides the dispersed light depending on change in angle of a reflection plane thereof.

10. The ophthalmic apparatus according to claim 1 further comprising a measurement optical system which makes measurement light converge at the fundus and photo-receives the measurement light reflected from the fundus on a second photodetector, and
wherein the calculation part obtains eye refractive power of the eye based on an output signal from the second photodetector.

11. The ophthalmic apparatus according to claim 10, wherein the first projection optical system and the measurement optical system share at least a light source.

12. The ophthalmic apparatus according to claim 10 further comprising a correction unit which corrects a position of at least a part of the measurement optical system based on the obtained eye refractive power in order to bring a convergence state of the measurement light at the fundus to a proper state.

* * * * *